US008627707B2

(12) United States Patent
Hardesty et al.

(10) Patent No.: US 8,627,707 B2
(45) Date of Patent: Jan. 14, 2014

(54) METHOD FOR THE DEVELOPMENT AND QUALITY CONTROL OF FLOW-OPTIMIZED SHAPED CHARGES

(75) Inventors: John Hardesty, Dallas, TX (US); Nathan G. Clark, Mansfield, TX (US); Matt R. Bell, Dallas, TX (US)

(73) Assignee: Geodynamics, Inc., Millsap, TX (US)

( * ) Notice: Subject to any disclaimer, the term of this patent is extended or adjusted under 35 U.S.C. 154(b) by 467 days.

(21) Appl. No.: 12/395,932

(22) Filed: Mar. 2, 2009

(65) Prior Publication Data

US 2009/0217739 A1 Sep. 3, 2009

Related U.S. Application Data

(60) Provisional application No. 61/032,130, filed on Feb. 28, 2008.

(51) Int. Cl.
*G01N 33/22* (2006.01)

(52) U.S. Cl.
USPC .......................................... 73/35.17; 102/306

(58) Field of Classification Search
USPC ......... 73/35.17, 35.14; 299/13; 102/303, 306, 102/331, 309, 313, 314
See application file for complete search history.

(56) References Cited

U.S. PATENT DOCUMENTS

| | | | | |
|---|---|---|---|---|
| 4,932,239 | A * | 6/1990 | Regalbuto | 73/35.14 |
| 5,251,561 | A | 10/1993 | Murphy | |
| 6,026,692 | A * | 2/2000 | Brovold | 73/818 |
| 6,644,099 | B2 | 11/2003 | Bell | |

FOREIGN PATENT DOCUMENTS

| | | | |
|---|---|---|---|
| JP | 05-332700 | A | 12/1993 |
| WO | WO 02-088622 | A1 | 11/2002 |

OTHER PUBLICATIONS

Authors: C. Ozgen Karacan and Phillip M. Halleck; Title: "Comparison of shaped-charge perforating induced formation damage to gas- and liquid-saturated sandstone samples"; Date: Apr. 16, 2003, Publisher: Elsevier Science, B.V.; Edition: Journal of Petroleum Science and Engineering, 40 (2003), pp. 61-64 of 61-75.*

Authors: B. Grove, J. Heiland, and I. Walton; Title: "Shaped Charge Penetration into Stressed Rock"; Date: Apr. 16-20, 2007; Publisher: 23rd International Symposium on Ballistics, Tarragona, Spain; pp. 1397-1400 of 1397-1403.*

Authors: unknown; Title: "Recommended Practices for Evaluation of Well Perforators, API Recommended Practice 19B", Date: Sep. 28, 2001, Publisher: American Petroleum Institute; 1st Edition and Errata 1.*

(Continued)

*Primary Examiner* — Lisa Caputo
*Assistant Examiner* — Roger Hernandez-Prewitt
(74) *Attorney, Agent, or Firm* — David W. Carstens; Carstens & Cahoon, LLP

(57) ABSTRACT

An improved test setup facility, referred to as a "Quick Development Cell" (QDC), which allows for rapid turnaround testing with valuable feedback to a design engineer. Because the QDC allows for quick and efficient testing at a sufficient frequency, QDC tests are compatible with production quality control. In addition to fostering improvement of the API's Section 2 type tests using stressed natural rock for benchmark experiments, the QDC tests allow for progress to be made towards the development of a flow-optimized shape charge and superior well performance.

13 Claims, 3 Drawing Sheets

190
160
150
140
180
130
170
120
110

(56) References Cited

OTHER PUBLICATIONS

Authors: Larry Behrmann, Andrew Brown, Phil Smith, David Underdown, et al.; Title: "Perforating Practices That Optimize Productivity"; Date: Mar. 1, 2000, Publication: Oilfield Review; vol: 12; Issue: 1; pp: 52-74; website: http://www.slb.com/resources/publications/industry__articles/oilfield__review/2000/or2000spr04__perforating__practices.aspx.*

Author, kherda, Title: "Compaction Rollers and Testing Equipment Work to Provide a Quality Road Surface", Date: Dec. 28, 2000, Publisher: Scranton Gillette Communications, Publication: Roads &Bridges, pp. 1-8, URL: http://www.roadsbridges.com/compaction-rollers-and-testing-equipment-work-provide-quality-road-surface.*

* cited by examiner

METHOD FOR THE DEVELOPMENT AND QUALITY CONTROL OF FLOW-OPTIMIZED SHAPED CHARGES

This application claims the benefit of and priority to U.S. Provisional Patent Application No. 61/032,130 filed Feb. 28, 2008, the technical disclosures of which is hereby incorporated herein by reference.

BACKGROUND OF THE INVENTION

1. Technical Field

The present invention relates to an improved facility for the testing, designing, and manufacturing of shaped charges optimized for flow performance in natural rock, as opposed to current standardized concrete targets. Specifically, the facility is capable of providing rapid, useful feedback from stressed natural rock targets, both during the charge design process and during manufacture in response to changing conditions and variations in raw materials.

2. Description of Related Art

Perforating systems utilizing shaped explosive charges have become the dominant method for connecting a cased-and-cemented completion to the desired reservoir interval. Due to the location of oil and gas within subterranean formations, one field that has benefited greatly from these perforating systems and their explosive charges is the production of oil and gas. Perforating systems are used to fracture the subterranean formations to increase their permeability, thereby increasing the rate at which the oil or gas can flow through the formation.

Before fracturing occurs, a well is bored into the formation. Individual lengths of relatively large diameter metal tubulars are secured together to form a casing string that is positioned within a subterranean well bore to increase the integrity of the well bore and provide a path for producing fluids from the formation to the surface. Conventionally, the casing is cemented to the well bore face and subsequently perforated by detonating shaped explosive charges. These perforations extend through the casing and cement a short distance into the formation. In certain instances, it is desirable to conduct such perforating operations with the pressure in the well being overbalanced with respect to the formation pressure. Under overbalanced conditions, the well pressure exceeds the pressure at which the formation will fracture, and therefore, hydraulic fracturing occurs in the vicinity of the perforations. As an example, the perforations may penetrate several inches into the formation, and the fracture network may extend several feet into the formation. Thus, an enlarged conduit can be created for fluid flow between the formation and the well, and well productivity may be significantly increased by deliberately inducing fractures at the perforations.

A shaped charge is an explosive device within which a metal shell called a liner, often conical or hemispherical, is surrounded by a high explosive charge, enclosed in a steel case. When the explosive is detonated, the liner is ejected as a very high velocity jet that has great penetrative power. Shaped charge performance has advanced considerably as the result of more potent explosives, tighter manufacturing tolerances, improved quality control, and overall design enhancements. However, it is well known that the flow path created by perforation with shaped charges is seldom ideal.

Research and development efforts to maximize the penetration capabilities of perforating systems and charges were based largely on trial and error when they were first introduced in the early 1950's, and although they were effective, for the most part, they were quite dangerous. It was not until the 1970s that modeling codes could predict with any accuracy how a shaped charge would behave. While the concept of a metal surface being squeezed forward may seem relatively straightforward, the physics of perforating systems utilizing shaped charges is very complex and even today, researchers recognize that extensive testing is required under simulated well conditions to satisfy the industry's need to predict perforator effectiveness. Consequently, industry standardization has been applied to effectively regulate perforating systems.

The American Petroleum Institute (API) issued its first recommended practice on the evaluation of wellbore perforators in the 1980's and the revised version, issued in 2001, sets out the currently accepted guidelines for perforator evaluation. These 2001 guidelines are divided into four sections, or procedures, to be used when representing perforating equipment performance to the oil & gas industry: 1) performance under ambient conditions, using a concrete target; 2) performance into stressed rock, using a Berea sandstone target; 3) performance at elevated temperature, using a steel target (for systems destined for high temperature deployment); and 4) flow performance under simulated downhole conditions.

Due to the variability of the properties of Berea sandstone and high costs associated with testing under simulated downhole conditions, concrete targets became the more favored standard on which to base equipment selection and purchasing decisions, resulting in tighter control on concrete formulation to improve overall uniformity. Accordingly, perforator manufacturers have focused on optimizing their products for maximum penetration into the prescribed concrete target. However, predicting downhole penetration using a concrete target is widely acknowledged as problematic since penetration is influenced by many different rock properties.

Any prediction on perforation flow performance based on Section 1 data is misguided due to the different rock properties in formations as well as the many factors that contribute to the flow performance of a perforation tunnel. Tunnel performance is the result of tunnel geometry and quality. Geometric effects include tunnel length and diameter. Quality effects include the distribution of material inside the tunnel, the condition of any material inside the tunnel, the condition of the tunnel side walls, tip geometry, and tunnel cracking. In addition, factors such as shaped charge design, target composition, target stress state, the initial relative pressure state between the wellbore and the formation (under, at or overbalanced), and the dynamic pressure events during perforation will each have an effect upon the geometry produced by a given perforating system.

Perforators optimized for maximum concrete penetration are highly unlikely to be optimized for maximum rock penetration and will not result in perforation geometry conducive to maximum flow. Research has in fact shown that the flow performance of charges optimized for a stressed rock target may be 10-15% greater than similar charges optimized for a cement target, with as much as 20% greater penetration into the rock target. For example, Table 1 (below) helps invalidate the API's Section 1 procedure as a legitimate benchmark by proving that some charges that perform well when tested in rock targets perform poorly when tested in cement targets.

TABLE 1

Performance of Charges Optimized for Rock or Cement.

| Target | Penetration (inches) | |
|---|---|---|
| | Charge A | Charge B |
| Cement Quality Control Target | 42.0 | 20.0 |
| Berea Sandstone Quality Control Target | 20.5 | 15.0 |
| Stressed Berea Sandstone Target | 10.6 | 11.4 |

Development of perforating systems using a concrete target is also misleading because it will drive the charge design towards the use of a suboptimal energy distribution, which is required to maximize penetration into concrete. As a result, this model of standardization forces the makers of perforating systems away from designs shown to deliver greater flow performance. To make matters worse, only 2-3 tests can be run in a normal work day under Section 2's established procedures for the testing of stressed rock targets, adding significant costs and delays when testing with rock targets versus the more accepted concrete targets currently used.

The quality control of shaped charges is also critical to ensuring product performance of perforating systems. Quality control processes provide important feedback to allow for the adjustment of the manufacturing of shaped charges in response to changing conditions and variations in raw materials. Quality control testing often leads to improved charge design, demonstrating a gradual re-optimization toward quality control target material. Predictive computer modeling can be useful in the early stages of development of a shaped charge, but an iterative process of testing and learning from design variations is the best way to achieve peak performance while gaining an understanding of the target rock formation. Consequently, there is a need for rapid testing procedures to provide for decreased operating and capital expenses in developing shaped charges. Further, there is a need to improve upon the API's Section 2 procedure for optimizing and standardizing perforating systems and charges using a stressed natural rock medium such that the flow path created by perforation of subterranean formations can be predicted more accurately. Further, there is a need for consistent production of these improved charges to achieve consistently improved well performance. Finally, there is a need for perforating systems that can also be rapidly customized to deliver maximum flow performance at specific field conditions, making region-, formation-, and even field-specific charge designs a realistic future goal.

SUMMARY OF THE INVENTION

Optimization for a stressed rock target has traditionally been prohibitively slow and costly due to the Section 2 type tests currently required by the American Petroleum Institute, which involve the use of stressed rock, specifically Berea sandstone, as a target. The improved test setup facility of the present invention, referred to herein as a "Quick Development Cell" (QDC), allows for rapid turnaround testing such that quick and efficient progress can be made towards the development of an optimized shape charge and favorable perforation geometry to maximize flow performance in natural rock.

Effective stress is applied to a rock target by pressuring the vessel while keeping pore and wellbore pressures at atmospheric conditions. Applied pressures of up to approximately 6,000 psi are typically sufficient to adequately represent downhole conditions. After optimizing the overall laboratory setup and test procedure, a significant number of tests can be completed each day, as compared to only two to three tests using the aforementioned conventional Section 2 Type apparatus. Subsequent measurements of the debris and effect on the materials are taken to design an optimal shaped charge.

The QDC offers use of an optimum target size for ease of handling and cost minimization, use of minimal consumables per test, rapid loading and unloading of the target, retention of standard charge configuration used for cement targets, the ability to apply representative effective stress to the target, and the ability for operation the QDC by a single technician.

Other aspects, embodiments and features of the invention will become apparent from the following detailed description of the invention when considered in conjunction with the accompanying drawings. The accompanying figures are schematic and are not intended to be drawn to scale. In the figures, each identical or substantially similar component that is illustrated in various figures is represented by a single numeral or notation. For purposes of clarity, not every component is labeled in every figure. Nor is every component of each embodiment of the invention shown where illustration is not necessary to allow those of ordinary skill in the art to understand the invention.

BRIEF DESCRIPTION OF THE DRAWINGS

The novel features believed characteristic of the invention are set forth in the appended claims. The invention itself, however, as well as a preferred mode of use, further objectives and advantages thereof, will be best understood by reference to the following detailed description of illustrative embodiments when read in conjunction with the accompanying drawings, wherein:

DETAILED DESCRIPTION

Figure 1:
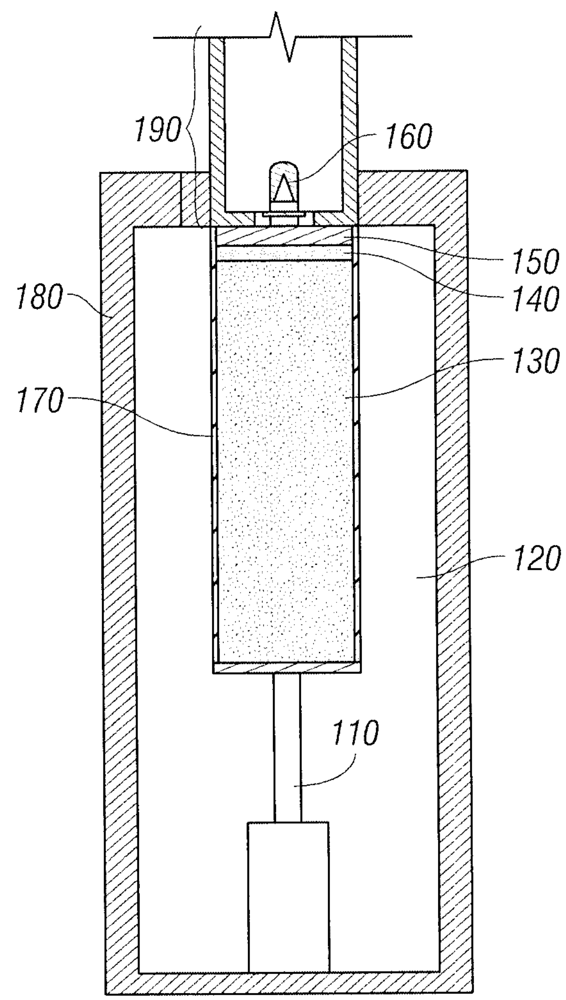
FIG. 1 is a cross-sectional view of the present invention.
Figure 2:
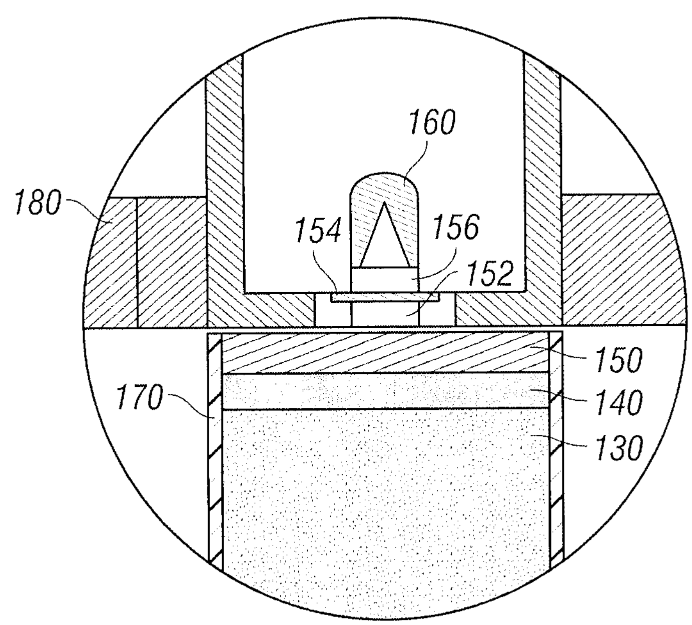
FIG. 2 is a close up view of the charge stack of the present invention

Using the improved vessel of the present invention, the rapid execution of tests into a stressed rock target is facilitated, making it possible to quickly and cost-effectively use such tests for development, quality control, and benchmarking purposes of evaluating perforating systems. FIG. 1 demonstrates a cross-sectional view of the improved vessel, hereinafter referred to as the "Quick Development Cell" (QDC). The target core ejection mechanism 110 is hydraulic cylinder based, which minimizes loading and unloading time and effort. In one embodiment, the rock target 130 is a cylindrical sample with a diameter of between approximately 4-6 inches, and more preferably 5 inches and a length of approximately 20-40 inches, and more preferably 24-36 inches. Sitting on top of the rock target 130, the cement plate 140 seals off the air from the inside of the chamber 180 and isolate the fluids and debris within the overburdening chamber 180, while the casing plate 150 aids in achieving correct placement of the cement plate 140. The rock target 130 and the cement and casing plates are surrounded by a flexible sleeve 170 to help minimize the amount of debris that is propelled into the surrounding chamber 180 upon detonation. FIG. 2 depicts a more detailed view of the charge stack 190. The charge stack 190 consists of: 1) a fluid filled clearance ring 152, which simulates the gun-to-casing clearance (also referred to as a "charge clearance spacer"), 2) a scallop plate 154, which simulates the gun wall, 3) an air filled standoff ring 156, which simulates the charge-to-gun clearance, 4) a shaped charge 160, and 5) a detonating cord and detonator (not pictured).

Figure 3:
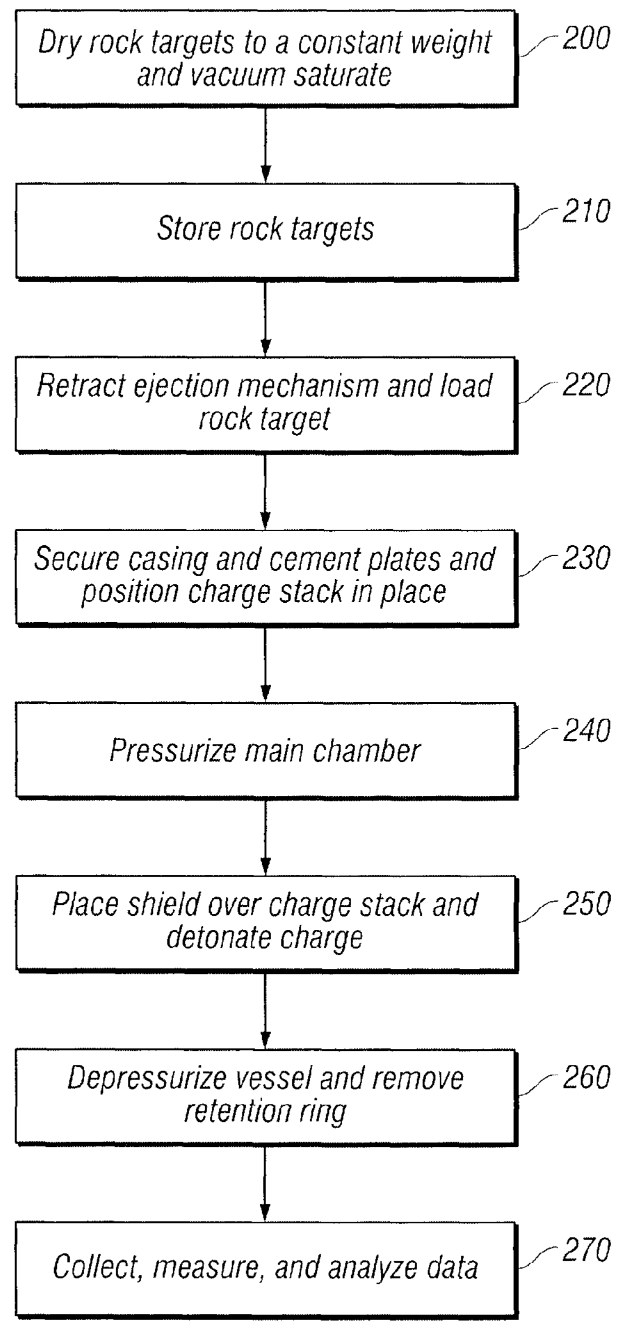
FIG. 3 is a flow chart representation depicting the overall process of one embodiment of the invention.

FIG. 3 illustrates the method for simulating the test on stressed rock targets and obtaining test data. Prior to testing, rock targets are dried to a constant weight and vacuum saturated (step 200), typically with odorless mineral spirits, followed by storage (step 210), according the API's recommendations. The ejection mechanism 110 is then retracted and the rock target 130 is loaded (step 220) through the top of the vessel. The casing plate 150 and cement plate 140 are placed on top of the rock target and secured in place by a retaining ring and a charge stack, described above, is placed on top of the target 130 (step 230). The main chamber 120 is then pressurized to between approximately 5,000 and approximately 7,000 psi, and more preferably to about 6,000 psi, applying axial and radial stresses to the rubber-sleeved core 170 (step 240). The wellbore chamber remains open to ambient conditions and the pore pressure system is vented to ensure complete saturation of the core and ambient pore pressure. A shield (not pictured) is placed over the charge stack to retain debris from the explosion and the charge is detonated (step 250). All debris is then collected for analysis. After depressurization of the vessel and removal of the retention ring (step 260), the collection, measurements, and analysis of data from the plates is performed. (step 270).

Casing and cement plates are collected for measurements of the casing and cement hole diameters. The target is then ejected and evaluated for probe depth, preferably using an 18" blunt probe. Target hole entry diameter is also measured as an indicator of optimum tunnel geometry and quality. Once these measurements are obtained, the core my be sawed and split by any means known in the art and further measurements such as penetration depth may be taken. One skilled in the art, armed with this disclosure, will recognize that a number of measurements and analysis can be performed. In one embodiment, for example, photographs showing the perforation geometry and quality are then optionally taken and may then be analyzed to provide a greater probability of correctly selecting the system most likely to deliver superior well performance and the quality control of shaped charges, including confirmation that production charges are delivering the correct perforation geometry. In another embodiment, computer modeling is used with any of the data collected including photographs and measurements and used in conjunction with the data to predict optimal shape charge performance.

Design iterations are tested and measurements are taken using the QDC until the observed tunnel geometry and quality imply good potential flow. Further, the design is tested in the flow cell, generally in accordance with the API's Section 4, to determine its flow performance relative to a baseline charge. In this way, expensive and time-consuming flow tests can be reserved for designs already showing promise in QDC testing. In trial runs, for example, the GEODynamics ConneX™ reactive perforating product line was tested using the QDC, which facilitated unprecedented levels of design iterations.

One skilled in the art, armed with this disclosure, will appreciate that there are countless ways to measure and utilize the data obtained from such simulated tests. It should be understood that the conditions of the conventional processing steps (e.g., list steps) may differ than those described herein, or other alternative processing steps may be used, as known to those of ordinary skill in the art. Further, the measurements undertaken after simulated explosive testing may vary in order to optimize the perforating system and the shaped charge performance based on the rock target used.

What is claimed is:

1. An apparatus for the rapid testing of shaped charges on a rock target, the apparatus comprising:

a) an overburdening chamber having an open end for accepting a rock target;

b) a retractable ejector located within the overburdening chamber at an end opposite to the open end, the ejector retracting to create a space for receiving of a rock target into the overburdening chamber;

c) a casing plate and a cement plate configured to cover the open end of the overburdening chamber; and d) a charge stack mounted to the overburdening chamber and creating a pressure seal for the overburdening chamber, wherein said charge stack comprises a clearance ring simulating gun-to-casing clearance and a standoff ring simulating charge-to-gun clearance;

whereby rapid removal of a rock target from the overburdening chamber is facilitated by the retractable ejector.

2. The apparatus of claim 1, wherein the rock target comprises natural rock.

3. The apparatus of claim 1, wherein the rock target comprises stressed rock.

4. The apparatus of claim 1, wherein the rock target comprises Berea sandstone.

5. The apparatus of claim 1 further comprising a sleeve for accepting the rock target.

6. The apparatus of claim 5 wherein the sleeve is flexible.

7. The apparatus of claim 1 further comprising a retaining ring for securing the cement plate and casing plate to the open end of the overburdening chamber.

8. A simulation method for the development of flow-optimized shaped charges and perforation geometry to maximize flow performance, said simulation method comprising the steps of:

retracting an ejector located within an overburdening chamber to create a space for insertion of a rock target within the overburdening chamber;

loading a rock target into the created space in the overburdening chamber;

sealing an open end of the overburdening chamber with a casing plate and a cement plate;

mounting a charge stack comprising a charge on an opposite side of the casing plate from the rock target;

pressurizing said overburdening chamber to simulate downhole conditions; and detonating the charge;

depressurizing said overburdening chamber; and ejecting the rock target with the ejector.

9. The method of claim 8, further comprising the step of:

collecting data from the detonation of said charge.

10. The method of claim 8, further comprising the step of:

unloading said rock target and repeating said method steps commencing with retracting the ejector to create a space for insertion of another rock target within the overburdening chamber.

11. The method of claim 8, wherein the pressurizing of said overburdening chamber occurs at approximately 6,000 psi.

12. The method of claim 8, further comprising surrounding the loaded rock target and said cement plate by a flexible sleeve.

13. An apparatus for the rapid testing of shaped charges on a rock target, the apparatus comprising:

a first chamber sized to receive a rock target therein, the first chamber having a first end sized for accepting a rock target;

a retractable ejector located within the first chamber at an end opposite the first end, the ejector retracting to create a space to receive a rock target into the first chamber;

a cement plate configured to face a contained rock target and seal off the first end of the first chamber;

a casing plate backing the cement plate;

a second chamber mounted to the first chamber around the casing plate, the second chamber creating a pressure seal for the first chamber, the second chamber comprising a charge stack, the charge stack having a first clearance ring simulating gun-to-casing clearance, and a second clearance ring simulating charge-to-gun clearance; and a sleeve configured to surround a rock target and to extend to the casing plate;

whereby rapid removal of a rock target after testing is facilitated by the retractable ejector.

* * * * *